United States Patent
Tomlinson et al.

(10) Patent No.: US 8,790,456 B2
(45) Date of Patent: Jul. 29, 2014

(54) POLYHYDROXY-DIAMINES AS MULTI-FUNCTIONAL ADDITIVES FOR PAINTS, COATINGS AND EPOXIES

(71) Applicants: Dow Global Technologies LLC, Midland, MI (US); Angus Chemical Company, Buffalo Grove, IL (US)

(72) Inventors: Ian A. Tomlinson, Midland, MI (US); Asghar A. Peera, Cary, IL (US)

(73) Assignees: ANGUS Chemical Company; Dow Global Technologies LLC

( * ) Notice: Subject to any disclaimer, the term of this patent is extended or adjusted under 35 U.S.C. 154(b) by 0 days.

(21) Appl. No.: 14/197,255

(22) Filed: Mar. 5, 2014

(65) Prior Publication Data
US 2014/0187678 A1 Jul. 3, 2014

Related U.S. Application Data

(62) Division of application No. 13/263,470, filed as application No. PCT/US2010/032701 on Apr. 28, 2007, now Pat. No. 8,702,859.

(60) Provisional application No. 61/173,619, filed on Apr. 29, 2009.

(51) Int. Cl.
*C09D 5/00* (2006.01)
*C09D 7/12* (2006.01)
*C09K 3/18* (2006.01)

(52) U.S. Cl.
USPC .............................................. 106/13; 252/70

(58) Field of Classification Search
USPC .............................................. 106/13; 252/70
See application file for complete search history.

(56) References Cited

U.S. PATENT DOCUMENTS

| | | | |
|---|---|---|---|
| 2,408,096 A | 9/1946 | Pierce et al. | |
| 2,828,277 A | 3/1958 | De Groote et al. | |
| 3,294,689 A * | 12/1966 | Pierce | 252/180 |
| 7,906,577 B2 * | 3/2011 | Zong et al. | 524/497 |
| 2010/0326320 A1 * | 12/2010 | Swedo et al. | 106/18.32 |

FOREIGN PATENT DOCUMENTS

| | | | |
|---|---|---|---|
| EP | 0297051 A2 | 12/1988 | |
| EP | 297051 A2 * | 12/1988 | G03C 1/68 |
| WO | 03/104337 A1 | 12/2003 | |
| WO | 2005/056515 A2 | 6/2005 | |
| WO | 2008/081036 A1 | 7/2008 | |
| WO | 2009/091592 A1 | 7/2009 | |

OTHER PUBLICATIONS

Kim, et al., Chemoselective N-acylatoin of Amino Alcohols Promoted by Magnesium Oxide in Aqueous Orgainc Solution, Tetrahedron Letters, vol. 43, No. 2, p. 277-279.

* cited by examiner

*Primary Examiner* — Michael J Feely

(57) ABSTRACT

Provided are polyhydroxy-diamine compounds of the formula I:

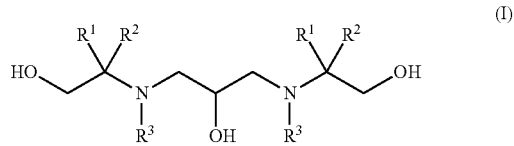

or salt thereof, wherein $R^1$, $R^2$, and $R^3$ are as defined herein. The compounds are useful as low additives for paints, coatings and epoxy formulations.

6 Claims, No Drawings

POLYHYDROXY-DIAMINES AS MULTI-FUNCTIONAL ADDITIVES FOR PAINTS, COATINGS AND EPOXIES

CROSS-REFERENCE TO RELATED APPLICATIONS

This application is a divisional of U.S. Ser. No. 13/263,470 (now U.S. Pat. No. 8,702,859), filed Oct. 7, 2011, which is a section 371 of PCT/US2010/032701, filed Apr. 28, 2010, which claims the benefit of U.S. Provisional application No. 61/173,619, filed Apr. 29, 2009.

FIELD OF THE INVENTION

The invention relates to polyhydroxy-diamine compounds and their use as additives for paints, coatings, and epoxy formulations. The polyhydroxy-diamine compounds are low odor, low volatile organic content (VOC) materials that provide a variety of functions in such formulations.

BACKGROUND OF THE INVENTION

Simple amine compounds are known to provide neutralizing, dispersant and/or hardening properties when used in paints and coatings and epoxy formulations. The simple amines, however, exhibit various shortcomings and undesirable properties when used in these applications and there is an ongoing need for new, next generation, solutions.

For instance, in many geographies, paint manufacturers are facing regulations to reduce the volatile organic content (VOC) of their formulations. Conventional neutralizing amines used in paint formulations are 100% volatile and are therefore VOC contributors. In addition, when used in an otherwise low VOC paint formulation, the odor of such amines is more noticeable. Efficient neutralizing agents, which both exhibit low or no VOC and have very low or no amine odor, would be a significant advance for the paints and coatings industry.

Paints and coatings are often subjected to widely varying temperatures, for instance during storage and transportation. Such varying temperatures may result in the paint or coating undergoing one or more freeze-thaw cycles. Freezing and thawing, however, has a detrimental effect on paint and coatings, unfavorably affecting their performance (e.g., by increasing the viscosity), and sometimes rendering the formulations unusable. Simple glycols (e.g., ethylene glycol) are sometimes included in paints and coatings with the purpose of providing freeze thaw stability. These materials, however, are often inadequate at providing the desired stability level. In addition, they may be high VOC materials and therefore generally not favored, particularly for use in low VOC formulations. New materials that address these concerns are desirable.

In the epoxy curing industry, many of the known amine-based hardeners currently used provide cured resins with limited adhesion stability. Replacement materials that can result in a resin with improved adhesion properties would be of value in the industry.

BRIEF SUMMARY OF THE INVENTION

In one aspect, the invention provides polyhydroxy-diamine compounds that are useful additives for paints, coatings, and epoxies. The compounds are of the formula I:

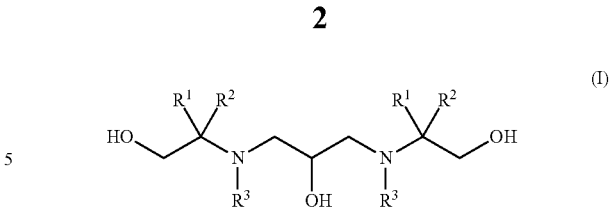

or salts thereof, wherein $R^1$, $R^2$, and $R^3$ are as defined herein.

In another aspect, the invention provides an aqueous based paint or coating comprising a binder, a carrier, a pigment, and a compound of formula I.

In a further aspect, the invention provides a curable resin system comprising an epoxy resin and a compound of formula I. The compound of formula I functions as a hardener and/or adhesion promoter.

In a further aspect, the invention provides a method for reducing the volatile organic compound content of an aqueous based paint or coating containing a binder, a carrier, and a pigment. The method comprises using, as a neutralizing agent and/or freeze-thaw stabilizer in the paint or coating, an effective amount of a compound of formula I.

In a further aspect, the invention provides a method for enhancing the freeze thaw stability of an aqueous based paint or coating, the method comprising including in the paint or coating: an effective amount of a compound of formula I.

In another aspect, the invention provides a method for making the compounds of formula I.

DETAILED DESCRIPTION OF THE INVENTION

As noted above, in one aspect the invention provides polyhydroxy-diamine compounds. The compounds are of the formula I:

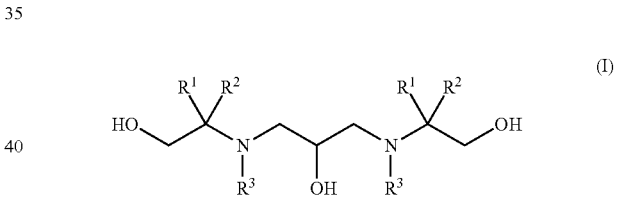

or salt thereof, wherein $R^1$ and $R^2$ are independently at each occurrence H, $CH_2OH$, $C_1$-$C_6$ alkyl; and $R^3$ is independently at each occurrence H or $C_1$-$C_6$ alkyl.

In some embodiments, $R^1$ in the compounds of formula I is, at each occurrence, $C_1$-$C_3$ alkyl or $CH_2OH$. In further embodiments, $R^1$ is methyl at each occurrence.

In some embodiments, $R^2$ is, at each occurrence, $C_1$-$C_3$ alkyl or $CH_2OH$. In further embodiments, $R^2$ is methyl at each occurrence. In still further embodiments, $R^3$ is H at each occurrence.

In some embodiments, when one of $R^1$ or $R^2$ is $CH_2OH$, then the other is H, or $C_3$-$C_6$ alkyl.

In some embodiments, $R^1$ and $R^2$ are, at each occurrence, $CH_2OH$. In some embodiments, $R^3$ at each occurrence is H.

In some embodiments, the compound of formula I is 2,2'-((2-hydroxytrimethylene)-diimino)bis(2-methyl-1-propanol) (i.e., $R^1$ and $R^2$ in formula I are methyl at each occurrence, and $R^3$ is H at each occurrence), 2,2'-((2-hydroxytrimethylene)-diimino)bis(2-ethyl-1,3-propanediol) (i.e. $R^1$ in formula I is ethyl, $R^2$ is hydroxymethyl ($CH_2OH$) and $R^3$ is H at each occurrence), 2,2'-((2-hydroxytrimethylene)-diimino)bis(2-hydroxymethyl-1,3-propanediol) (i.e. $R^1$ and $R^2$ in formula I are hydroxymethyl and $R^3$ is H at each occurrence), 2,2'-(2-hydroxypropane-1,3-diyl)bis (azanediyl)bis(2-methylpropane-1,3-diol) (i.e. $R^1$ in formula I is methyl, $R^2$ is hydroxymethyl ($CH_2OH$) and $R^3$ is H at each occurrence), or 2,2'-(2-hydroxypropane-1,3-diyl)bis (azanediyl)dipropane-1,3-diol ($R^1$ is $CH_2OH$ at each occurrence) and $R^2$ and $R^3$ are H at each occurrence).

The compounds of formula I may be used in the form of acid salts. Suitable salts include, but are not limited to, hydrochloric acid, boric acid, lactic acid, pelargonic acid, nonanoic acid, neodecanoic acid, sebacic acid, azelaic acid, citric acid, benzoic acid, undecylenic acid, lauric acid, myristic acid, stearic acid, oleic acid, tall oil fatty acid, ethylenediaminetetraacetic acid and like materials.

The compounds of formula I may be used as neutralizing agents in aqueous-based paint and coating formulations. Neutralizing agents are included in such formulations to raise the pH to a desired value, typically between about 8 and 10. Conventional neutralizing agents currently used in the industry are VOC contributors. In addition, when used in an otherwise low VOC formulation, the odor of conventional neutralizing agents is more noticeable.

In contrast, the compounds of the invention are excellent low odor materials with the benefit of having no or very low VOC. For instance, as demonstrated by the Examples, 2,2'-((2-hydroxytrimethylene)-diimino)bis(2-methyl-1-propanol), 2,2'-((2-hydroxytrimethylene)-diimino)bis(2-ethyl-1,3-propanediol) and 2,2'-((2-hydroxtrimethylene)-diimino) bis(2-hydroxymethyl-1,3-propanediol), exemplary compounds of the invention, are no or low VOC contributors.

In addition to their excellent low VOC and low odor attributes, the compounds of the invention also permit for higher pH formulations to be achieved without addition of significantly larger quantities of the material relative to the entire formulation, thus permitting conservation of materials. Further, the compounds of the invention are effective dispersants for pigment particles present in paint and coating formulations, thus serving dual roles in the formulation and consequently again conserving materials.

In addition to functioning as low VOC neutralizing agents in aqueous based paints and coatings, the polyhydroxy-diamine compounds of the invention have also been discovered to function as low VOC enhancers of freeze-thaw stability in such systems. Thus, in a further aspect, the invention provides aqueous based paints and coatings comprising a compound of formula I as a freeze thaw stability enhancer. Freeze thaw additives are added to paint and coating formulations to depress the freezing point and therefore to allow the formulations to maintain their desired properties, including viscosity, even after exposure to temperature variation, particularly temperatures that would cause freezing and thawing. When such additives are absent, the paint may flocculate and/or have increased viscosity which may make them difficult to use. In some cases, formulations may solidify, rendering them unusable. The compounds of formula I provide freeze thaw stability enhancement with the added benefit of being low or no VOC materials. Thus, the compounds are effective replacements for higher VOC freeze-thaw additives, such as glycols.

When used as a free thaw enhancing additive, the polyhydroxy-diamines are added late in the formulation (e.g., during the letdown phase of the manufacturing process, described below). In this embodiment, the polyhydroxy-diamine functions primarily as a freeze thaw stabilizer and secondarily as a neutralizer for final pH adjustment.

Particularly improved freeze thaw stability is observed upon incorporating a compound of formula I in which $R^1=R^2=CH_2OH$. In addition, paints and coatings containing compounds of formula I where $R1=R2=CH_2OH$, in general, exhibit higher equilibrated pH values (about 0.1-0.2 pH units higher than without the post-add), leading to greater freeze thaw stability.

In some embodiments, the compounds of formula I may be used in combination with other freeze-thaw co-additives to further enhance the stability of a formulation. Co-additives for this combination embodiment include, for example, the freeze-thaw stabilizers disclosed in PCT International Patent Publication WO 2009/091592, which is incorporated herein by reference in its entirety. Preferred co-additives include ethoxylated tristerylphenolic compounds having the following formula A:

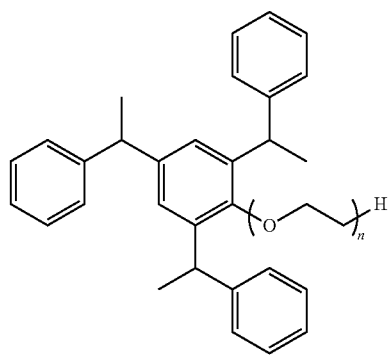

wherein n is 6-60, alternatively 8-50, or alternatively 8-25. In some embodiments, the ratio of the compound of formula I to the co-additive freeze thaw agent, such as formula A compounds, may be between about 10:1 and about 1:1, alternatively between 6:1 and 2:1. If the compound of formula I is also included in the formulation as a neutralizer, as described above, then that amount of the compound used as neutralized is not calculated in the foregoing ratios.

In a further aspect, the invention provides an aqueous based paint or coating in which a compound of formula I is present as a neutralizing agent and/or freeze-thaw stabilizer. The paint or coating is used to provide a protective and/or decorative barrier for residential and industrial surfaces, such as for floors, automobiles, exteriors and interiors of houses, and other buildings. According to this aspect of the invention, the paint or coating formulation, in addition to comprising a compound of formula I, also comprises a binder, a pigment, and a carrier.

Pigments are included to provide the desired color to the final coated material and may also be used to provide bulk to the paint or coating. While multiple pigments may be present in end-use paints or coatings, sometimes only a white pigment, such as a zinc oxide and/or a titanium oxide, is added in the early stages of the formation of the formulation. Any other desired pigments of various colors (including more white pigment) can optionally be added at the later stages of, or after, the formulation is formed.

Pigments may be organic or inorganic. Examples of pigments can include, but are not limited to, titanium dioxide, kaolin clay, calcined kaolin clay, carbon black, iron oxide black, iron oxide yellow, iron oxide red, iron oxide brown, organic red pigments, including quinacridone red and metallized and non-metallized azo reds (e.g., lithols, lithol rubine, toluidine red, naphthol red), phthalocyanine blue, phthalocyanine green, mono- or di-arylide yellow, benzimidazolone yellow, heterocyclic yellow, quinacridone magenta, quinacridone violet, and the like, and any combination thereof.

Binders are included in the paint and coating formulations to provide a network in which the pigment particles are dispersed and suspended. Binders bind the pigment particles together and provide integrity and adhesion for the paint or coating film. Generally, there are two classes of binders: latex binders are used in aqueous based formulations, and alkyd-based binders are used in non-aqueous formulations, ultimately resulting in latex paints and coatings and alkyd paints and coatings, respectively.

In latex based paint and coating formulations, the binders are typically prepared by free radical initiated aqueous emulsion polymerization of a monomer mixture containing alkyl acrylate (methyl acrylate, ethyl acrylate, butyl acrylate and/or 2-ethylhexylacrylate), alkyl methacrylate, vinyl alcohol/acetate, styrene, and/or acrylonitrile and ethylene type monomers. The amount of the binder in the formulations of the invention can be the amount conventionally used in paint and coating formulations. By way of non-limiting examples, the amount of binder solids may be from about 2% to about 75%, alternatively from about 5% to about 65%, or alternatively from about 20% to about 55%, by weight based on the total weight of the formulation.

The formulations also contain a carrier in which the formulation ingredients are dissolved, dispersed, and/or suspended. In the aqueous based formulations of the invention, the carrier is usually water, although other water-based solutions such as water-alcohol mixtures and the like may be used. The aqueous carrier generally makes up the balance of the formulation, after all the other ingredients have been accounted for.

Other additives may be included in the paint and coating formulations besides the polyhydroxy-diamines, pigments, binders, and carriers discussed above. These include, but are not limited to, leveling agents and surfactants, thickeners, rheology modifiers, co-solvents such as glycols, including propylene glycol or ethylene glycol, corrosion inhibitors, defoamers, co-dispersants, additional aminoalcohol compounds, and biocides.

The paint and coating formulations of the invention may be manufactured by conventional paint manufacturing techniques, which are well known to those skilled in the art. Typically, the formulations are manufactured by a two-step process. First, a dispersion phase, commonly referred to as the grind phase, is prepared by mixing the dry pigments with other grind phase components, including most other solid powder formulation materials, under constant high shear agitation to provide a high viscosity and high solids mixture. This part of the process is designed to effectively wet and dis-agglomerate the dry pigments and stabilize them in an aqueous dispersion.

The second step of the paint manufacturing process is commonly referred to as the letdown or thindown phase, because the viscous grind is diluted with the remaining formulation components, which are generally less viscous than the grind mix. Typically, the binders, any predispersed pigments, and any other paint materials that only require mixing and perhaps moderate shear, are incorporated during the letdown phase. The letdown phase may be done either by sequentially adding the letdown components into a vessel containing the grind mix, or by adding the grind mix into a vessel containing a premix of the latex resins and other letdown components, followed by sequential addition of the final letdown components. In either case, constant agitation is needed, although application of high shear is not required. The compounds of formula I of the invention are typically added to the formulation at one or more of three different places in the manufacturing process: to the pigment dispersion, to the binder dispersion, and/or in a final addition to the paint formulation.

When used primarily as a neutralizer, the amount employed is determined based on the desired pH of the formulation. Typically, an amount of the compound is added so as to provide a final pH in the range of about 8 and 10, more preferably about 8.5 to 9.5. When used primarily as a freeze-thaw additive, the amount of the polyhydroxy-diamine compound is, in some embodiments, from about 0.01 to about 5%, based on total weight of the formulation. In further embodiments, the amount is between about 0.01 and about 2.

In a further aspect, the invention provides a method for reducing the volatile organic compound content of an aqueous based paint or coating that contains a binder, a carrier, and a pigment. The method comprises using as the neutralizing agent and/or freeze-thaw stabilizer an effective amount of a compound for formula I. As noted above, an effective amount is the quantity required to provide a pH of about 8 to 10, preferably 8.5 to 9.5, in the paint or coating formulation.

In a still further aspect, the compound of formula I may be used as hardeners for epoxy coatings and have been found to improve the adhesion of fusion bonded epoxy (FBE) coatings to metal substrates in standard and low temperature fused FBE. Thus, according to this aspect of the invention, a curable resin is provided that comprises 35 to 90% by weight of an epoxy resin and 0.1 to 35% by weight of a compound of formula I, based on the total weight of the resin formulation.

The compounds of formula I may also allow formulators to use lower application temperature due to lower melting points of these hardeners relative to highly crystalline hardeners. The polyhydroxy-diamine compounds may further allow enhanced resistance to cathodic disbondment (CD) and provide toughened FBE coatings.

Curable epoxy resin systems may be formed by admixing at least one epoxy resin, the polyhydroxy-diamine described hereinabove, as well as, optionally, a catalyst, other hardeners, toughening agents, flame retardants, fillers and other additives known and used by persons of ordinary skill in the relevant art. The curable epoxy resin system may then be cured, for example, without limitation and dependent upon the particular type of epoxy resin used and its intended application, by exposure to elevated temperatures, exposure to ultraviolet light, etc.

As is familiar and well within the ability of persons of ordinary skill in the relevant art, amounts up to the stoichiometric amount of the polyhydroxy-diamine hardener, relative to the epoxy resin, are considered "effective amounts" in accordance with the present invention. More particularly, the stoichiometric amount of the polyhydroxy-diamine hardener is calculated by adding together the number of equivalents on the basis of weight per displaceable —NH group in the polyhydroxy-diamine utilized. Generally, as is also understood by persons of ordinary skill, a lesser amount of a polyhydroxy-diamine hardener of higher molecular weight will be required than of a polyhydroxy-diamine hardener of lower molecular weight.

The diamino alcohols can be used with any type of epoxy resin, which means, as that term is used herein, compounds containing one or more reactive oxirane groups (—$C_2H_3O$), referred to herein as "epoxy groups" or "epoxy functionality". Suitable epoxy resins include those compounds containing at least one vicinal epoxy group. The epoxy resin may be saturated or unsaturated, aliphatic, cycloaliphatic, aromatic or heterocyclic and may be substituted. The epoxy resin may also be monomeric or polymeric.

More particularly, epoxy resins suitable for use in accordance with the present invention include, for example without limitation, cycloaliphatic (acyclic) epoxides, cycloaliphatic epoxides modified with glycols, epoxy phenolic novolac resins, multifunctional (polyepoxy) epoxy resins, bisphenol A-based epoxy resins, and bisphenol F-based epoxy resins, among others, as well as mixtures thereof. These materials can be used with other hardeners and/or catalyst systems depending on the application. The material can also be used as a 'modified hardener' or prepolymer by reacting it, initially, with LER (liquid epoxy resin) and then using the reaction product in the final epoxy resin formulation.

In a still further aspect, the invention provides a method for making the compounds of formula I. The method comprises reacting an epoxide compound of formula (III):

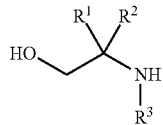
(III)

wherein X is a leaving group, with two or more equivalents of an aminoalcohol compound of formula (II):

(II)

wherein $R^1$, $R^2$, and $R^3$ are as defined above, to provide a compound of formula I or salt thereof.

Suitable leaving groups, X, in the formula (III) compounds include halogens, mesylate or tosylate. Preferred is Cl.

The reaction between the formula (III) epoxide and the formula (II) aminoalcohol is carried out neat or in a solvent. Non-limiting examples of suitable solvents include water and alcohols such as methanol or ethanol. The reaction is highly exothermic and can be more readily controlled by heating at reflux. Once the reaction has achieved the desired level of completion, a base, such as NaOH is added to convert any acid salts of the compound to the neutral compound. Conventional workup may be used to isolate the desired compound, such as crystallization, filtration, distillation, evaporation and/or chromatography.

The term "alkyl" as used herein, means a straight or branched chain hydrocarbon containing the indicated number of carbon atoms. If no number is indicated, then alkyl contains from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The following examples are illustrative of the invention but are not intended to limit its scope. Unless otherwise indicated, ratios, percentages, parts, and the like used herein are by weight.

EXAMPLES

Example 1

Synthesis of 2,2'-((2-hydroxytrimethylene)diimino) bis(2-methyl-1-propanol)(1)

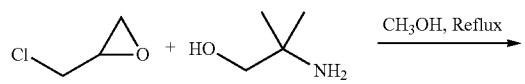

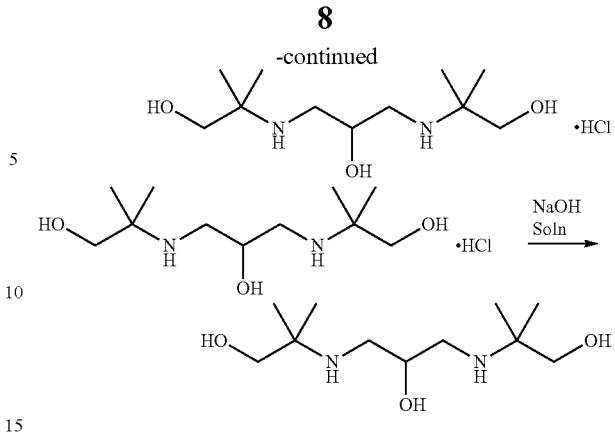

A 3 neck round bottom flask equipped with a stir bar, dropping funnel, condenser and nitrogen outlet is charged with 52.3 g, (0.56 mol) of 2-amino-2-methyl-1-propanol (used as a 95% aqueous solution). To this colorless solution is added epichlorohydrin (22 mL, 0.28 mol.) drop wise via an addition funnel at room temperature. The reaction mixture is stirred and after complete addition of epichlorohydrin and constant stirring for about 5 minutes, a large exotherm is observed. The colorless solution turns to a high viscous pale yellow material. At this point stiffing is stopped and approximately 200 mL of methanol are added to the mixture to decrease the viscosity of the material and to resume stirring. The content of the flask is refluxed for 6-10 hrs until the disappearance of the starting materials.

The reaction is stopped and excess methanol removed by rotary evaporator. The resulting material is dissolved in sodium hydroxide/methanol solution. The transparent yellow solution turns cloudy and after few minutes a white solid crashes out of the solution. This white solid collected is the sodium chloride salt formed during the acid base reaction. The salt is separated from the solution by gravity filtration and the methanol solution is dried over anhydrous magnesium sulfate and filtered. The solvent is removed by rotary evaporator and a yellow solid crashes out once all the solvent is removed. The yellow solid is recrystallized in methanol and resulting white solid is air dried followed by drying in vacuo at 60° C. for 5 h. Approximately 39.2 g (60%) of the desired compound 1 is obtained after drying in vacuo. GC analysis indicates >99% purity. $^1$H NMR (MeOD-$d_4$): a 1.05 (broad s, 12H), a 2.53-2.60 (m, 4H) and a 3.26-3.35 (m, 4H), a 3.72 (m, 1H). $^{13}$C NMR (MeOD-$d_4$): a 33.3, 33.9, 57.4, 65.0, 79.1 and 81.2 ppm. CI-MS: [MH]$^+$ m/z: 235. The melting point for the solid is 118-121° C.

Example 2

Synthesis of 2,2'-((2-hydroxytrimethylene)-diimino)-bis(2-hydroxymethyl-1,3-propanediol) (2)

A 250 mL 3 neck round bottom flask equipped with a stir bar, dropping funnel, condenser and nitrogen outlet is charged with 2-amino-2-(hydroxymethyl)propane-1,3-diol (50.0 g, 0.413 mols) and dissolved in methanol (30 mL). The slurry is warmed up until all of the triol dissolves. To this colorless solution is added epichlorohydrin (19.0 g, 0.205 mols) drop wise via a dropping funnel at room temperature. The reaction mixture is stirred and after complete addition of epichlorohydrin and constant stiffing for about 5 minutes, a slight exotherm is observed. The content of the flask is refluxed for 12 hrs until the disappearance of the epichlorohydrin. At this point the reaction is stopped and excess methanol removed by rotary evaporator. The resulting material is highly viscous.

The material is dissolved in methanol and to this is added sodium hydroxide/methanol solution. The transparent colorless solution turns cloudy and after few minutes a white solid crashes out of the solution. The white solid (sodium chloride salt formed during the acid base reaction) is separated from the solution by gravity filtration. The filtrate is kept at room temperature for an additional 30 minutes to allow additional sodium chloride not removed after the first filtration to crash out of solution. The resulting methanol solution is dried over anhydrous magnesium sulfate and filtered. The solvent is removed by rotary evaporator and a white wet material is obtained. The material is air dried followed by drying in vacuo at 60° C. for 5 h. Approximately 44 g (72%) of the desired compound 2 is obtained after drying in vacuo. The desired product is confirmed by NMR and HPLC-MS. $^{13}$C NMR (MeOD-$d_4$): ∂ 56.5, 71.0, 72.7 and 82.2 ppm. LC-MS: [1\4H]$^+$ m/z: 299. The extra peaks on NMR at 68.0 and 74.8 ppm correspond to residual starting triol remaining in the mixture.

Example 3

Synthesis of 2,2'-(2-hydroxypropane-1,3-diyl)-bis (azanediyl)bis(2-methylpropane-1,3-diol) (3)

A 500 mL 3 neck round bottom flask equipped with a stir bar, dropping funnel, condenser and nitrogen outlet is charged with 2-amino-2-methylpropane-1,3-diol (60.0 g, 0.571 mols) and dissolved in water (70 mL). The mixture is stirred until a clear solution is obtained. To this colorless solution is added epichlorohydrin (25.0 g, 21.2 mL, 0.272 mols) drop wise via a dropping funnel at room temperature. The reaction mixture is stirred and after complete addition of epichlorohydrin and constant stiffing, an exotherm is observed. The content of the flask is refluxed for 12 hrs until the disappearance of the epichlorohydrin. At this point the reaction is stopped and excess methanol removed by rotary evaporator. The resulting material is highly viscous.

The material is dissolved in methanol and to this is added sodium hydroxide/methanol solution. The transparent colorless solution turns cloudy and after few minutes a white solid crashed out (the sodium chloride salt formed during the acid base reaction). The salt is separated from the solution by gravity filtration. The filtrate is kept at room temperature for additional 30 minutes to allow additional sodium chloride not removed after the first filtration to crash out of solution. The resulting methanol solution is dried over anhydrous magnesium sulfate and filtered. The solvent is removed by rotary evaporator and a viscous wet material is obtained. This is air dried followed by drying in vacuo at 60° C. for 6 h. Approximately 54.3 g (74%) of the desired compound 3 is obtained after drying in vacuo. The desired product is confirmed by HPLC-MS. LC-MS: [MH]$^+$ m/z: 269.

Example 4

Efficacy as a Neutralizing, Co-dispersing Amine in a Paint Formulation

The compound of Example 1 is tested as a neutralizing, co-dispersing amine and compared relative to commercial neutralizers in an aqueous based, latex semi-gloss formulation. The comparative neutralizers 2-amino-2-methyl-1-propanol (AMP): 2-amino-2-ethyl-1,3-propane-diol (AEPD): N-butyl-diethanolamine (NBDA).

The paint formulation in which the compounds are tested is latex based semi-gloss material containing:

Pigments such as titanium dioxide (e.g., TIPURE® R942 from DuPont) and ground calcium carbonate (e.g., OMYACARB® UF from Omya, Inc.) (total of both pigments 20-25%).

Binder such as UCAR™ Latex 379 and 6030 from The Dow Chemical Company (total of both binders 40-45%).

Thickeners and rheology modifiers such as hydroxyethylcellulose (e.g., CELLOSIZE™ HEC from Dow) and solvent-free, non-ionic associative thickening agent/hydrophobically modified polyethylene oxide urethane—HEUR (ACRYSOL™ RM-5000 from Rohm and Haas) (total of both thickener (3-5%).

Neutralizer or amine such as AMP (comparative), or Compound 1 (inventive) (0.2-2%).

The pH, particle size, film opacity, gloss, and VOC of the formulations containing the various tested compounds are determined as follows:

Coating Optical Properties (Opacity and Gloss). The opacity, gloss at 20, 60, and 85° and color of the dried films is measured using an automated color/gloss/thickness robot based on a Symyx XCM module. The color is measured using an Ocean Optics ISP-REF integrating sphere with a 0.4" sampling aperture connected by a fiber optic cable to an Ocean Optics USB 4000 Spectrometer. Measurements are performed with D65 illumination. This apparatus is located on the left arm of a Symyx Core Module Robot which enables the colorimeter to be moved onto the sample in multiple locations. For this study measurements are done on three separate areas on both the black and white parts of each Leneta paper. The gloss is measured using a BYK micro-Tri-gloss Meter. This instrument is attached to the right arm of the Symyx Core Module Robot, along with a plate gripper used to move the samples from the BenchCel sample hotel to the deck of the Module. Gloss is measured in three different spots on the coatings over both the white and black parts of the Leneta paper.

Particle Size Analysis.

The particle size distribution in the formulations is measured using a Beckman Coulter LS-230 Particle Size Analyzer using a Micro-Volume Accessory. One drop of the formulation is added to approximately 20 mL of deionized water, and shaken well. This diluted solution is then added drop wise to the micro-volume accessory by pipet until the absorbance reading is at least 8%. The sample is stirred continuously during the measurement. Particle sizes from 0.04 to 2000 microns can be detected. The particle size distribution of a garnet standard with nominal particle size 35 microns is measured to be 36±15 microns.

pH Measurements.

The formulation pH is measured using a Fisher Scientific Accumet 15 pH meter, equipped with a ThermoElectron Orion 9203BN combination pH electrode. Commercial pH buffers are used to calibrate the equipment before each use. The reported values are the average of three separate reading on each formulation, the probe is cleaned with DI water between each measurement.

Volatile Organic Content (VOC).

VOC may be measured as follows. The amines are weighed in a pan and kept in an oven for 1 h at 105-110° C. The percent weight loss is reported as the VOC, corrected for the water content in the sample which can be measured by Karl Fisher Titration. The VOC contribution of only the neat amines is measured using this test. In a paint formulation, the amine may be in the form of a neutralized salt and may exhibit lower volatility.

Another test for determining VOC is by a GC method. This method is emerging in the industry as a preferred technique for designating a paint component either as a VOC contributor or as a no VOC contributor. According to this method, 280° C. is used as the cut off for determining which materials are VOC. Individual components are injected in the GC to observe their retention time. The retention time of the materials are noted with respect to a marker with a know boiling point of 280° C. Materials that elute before the marker in the GC are considered VOC and ones that are retained longer than the marker in the GC column are considered no VOC. Typical GC conditions include: DB-5 Column, Initial Temp: 75° C., Initial Time: 1 min, Final Temp: 280° C., Final Time: 5 min, Rate: 10° C./min, Front Inlet Temp: 250° C. and Front Detector Temp: 280° C.

The data are shown in Table 1.

TABLE 1

| Compound | Formulation pH | Particle Size | Film Opacity | Gloss | GC Retention Time (min) | VOC of Material |
|---|---|---|---|---|---|---|
| Cmpd 1[1] | 9.1 | 0.610 | 97.6 | 28.4 | 22.88 | 2.4% |
| AMP[2] | 9.1 | 0.617 | 97.3 | 30.0 | 5.56 | 100% |
| NBDA[2] | 9.0 | 0.622 | 97.1 | 30.3 | 15.30 | 21% |
| AEPD[2] | 9.0 | 0.620 | 97.7 | 31.2 | 11.72 | 9.1% |
| Marker | — | — | — | — | 19.30 | — |

[1]Compound of the invention prepared as described in Example 1.
[2]Comparative neutralizer.

As can be seen from the results, Compound 1 performs comparable to the three commercial products, AMP, NBDA and AEPD, achieving good co-dispersion of the pigment (as represented by the particle size analysis) which translates into good film opacity and gloss measurements. In addition, Compound 1 is a no or low VOC material according to both tests used. Compound 1 also has a negligible odor, thus addressing the concerns with some known neutralizers in low VOC paint formulations.

Example 5

Freeze-Thaw Evaluation Study in a Low VOC Semi-Gloss Paint

Table 2 provides data on the evaluation of compounds of the invention as freeze thaw stability enhancers. Formulations 1 and 2 in the Table relate to the invention. Abbreviations used are as follows.

Cmpd 2=compound of the invention prepared as described in Example 2 above.
KU=Viscosity measurement reported in Krebs units
ICI=High shear viscosity measurement
Acrysol™ RM-5000: non-ionic urethane rheology modifier
Acrysol RM-895: Nonionic Rheology Modifier
FT-100 refers to a freeze thaw surfactant from Rhodia available as RHODOLINE® FT100
BOPS: Based On Polymer Solid
Total RM wt: Total amount of Rheology Modifier
Strodex TH 100/A-34 is a surfactant sold by Hercules
Na=material contains solids, so viscosity cannot be measured

TABLE 2

| Paint ID | Formulation 1 | Formulation 2 | Formulation 3 | Formulation 4 |
|---|---|---|---|---|
| Polymer ID | Acrylic copolymer | Acrylic copolymer | Acrylic copolymer | Acrylic copolymer |
| Grind Surfactant | Strodex TH-100/A-34 | Strodex TH-100/A-34 | Strodex TH-100/A-34 | Strodex TH-100/A-34 |
| Neutralizer | NBDA | NBDA | NBDA | AEPD |
| Neutralizer Wt (lbs/100 gal) | 4.1 | 4.1 | 4.1 | 3.06 |
| Post-Add | 0.875% FT-100 (BOPS) | 0.875%[4] FT-100 + 2.3% Cmpd 2 (BOPS) | 0.875% FT-100 + 4.6% Cmpd 2 (BOPS) | 0.875% FT-100 (BOPS) |
| Post-Add Wt (lbs/100 gal) | FT (2.16) | FT (2.16), PHDA (5.0) | FT (2.16) PHDA (10.0) | FT (2.16) |
| Optifilm % | 3 | 3 | 3 | 3 |
| ICI Build | Acrysol RM-5000 | Acrysol RM-5000 | Acrysol RM-5000 | Acrysol RM-5000 |
| ICI Build Wt (lbs/100 gal) | 40 | 40 | 40 | 40 |
| KU Build | Acrysol RM-895 | Acrysol RM-895 | Acrysol RM-895 | Acrysol RM-895 |
| KU Build Wt (lbs/100 gal) | 3.0 | 3.0 | 3.0 | 3.0 |
| Total RM Wt. | 43 | 43 | 43 | 43 |
| Initial KU | 96 | 94 | 94 | 96 |
| Initial ICI | 1.3 | 1.3 | 1.3 | 1.40 |
| Initial pH | 8.80 | 8.98 | 9.05 | 8.80 |
| Equil. KU | 98 | 96 | 96 | 100 |
| Equil. ICI | 1.3 | 1.3 | 1.3 | 1.4 |
| Equil. pH | 8.83 | 9.06 | 9.13 | 8.85 |
| ΔKU | 2 | 2 | 2 | 4 |
| ½ pt KU (Int.) | 99 | 97 | 98 | 101 |
| Freeze/Thaw | | | | |
| Cycle 1 (KU) | >140 | 114 | 111 | >140 |
| Cycle 2 (KU) | >140 | 116 | 112 | >140 |
| Cycle 3 (KU) | >140 | 115 | 107 | >140 |
| Cycle 4 (KU) | >140 | 117 | 110 | >140 |
| Cycle 5 (KU) | >140 | 119 | 108 | >140 |
| ΔKU Max | na | 19.2 | 11.6 | na |

Formulations 2 and 3 both contain compound 2 (of the invention) as a post add. Only a slight/moderate gain in the viscosity is observed with these formulations following the freeze thaw cycles. In contrast, non-inventive formulations 1 and 4 shown extremely high viscosity beyond 140 KU.

Example 6

Epoxy Formulation

A fusion bonded epoxy (FBE) powder coating formulation is prepared by compounding DER 664UE (a Bisphenol A based resin); DEH 82 (a hydroxyl group containing Bisphenol A base crosslinker); Epikure 101 (ultra-rapid curing epoxy powder coating converter); Vansil W 20 (Calcium metasilicate; reinforcing filler); Modaflow Powder III (flow enhancing additive); and compound 3 (see Example 3). The resulting FBE powder coating is applied, using a fluidizing bed, on a heated bar and panels at 232° C. and cured in an oven at 232° C. for 2 minutes. After curing, the bars and panels are quenched on tap water at room temperature. The final coatings thickness is 15 mills Table 3 below summarizes the cathodic disbondment (CD) data for formulations treated with compound 3 (inventive) in comparison to an untreated formulation (control).

In the CD testing, coated samples are exposed to 3% NaCl solution at a known current for several days (from 7-28 days) in order to reproduce corrosive conditions. The coating is then delaminated manually by leveraging movement with a blade. The adhesion performance is rated by the size of the non delaminated area.

TABLE 3

| Time to failure the CD test 7 days @ 65° C. and −3.5 v. | | |
|---|---|---|
| | Control No additives | Cmpd 3 |
| Delamination in mm | 11 | 6 (45% improvement in CD) |

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A method for enhancing the freeze thaw stability of an aqueous based paint or coating, the method comprising including in the paint or coating:
   (a) an effective amount of a compound of formula I:

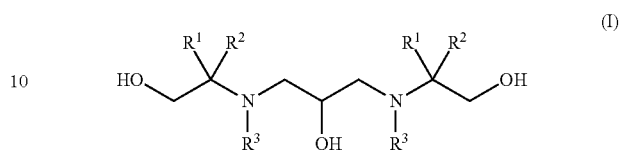

wherein $R^1$ and $R^2$ are independently at each occurrence H, $CH_2OH$, $C_1$-$C_6$ alkyl; and $R^3$ is independently at each occurrence H or $C_1$-$C_6$ alkyl; and
   (b) an effective amount of a compound of formula A:

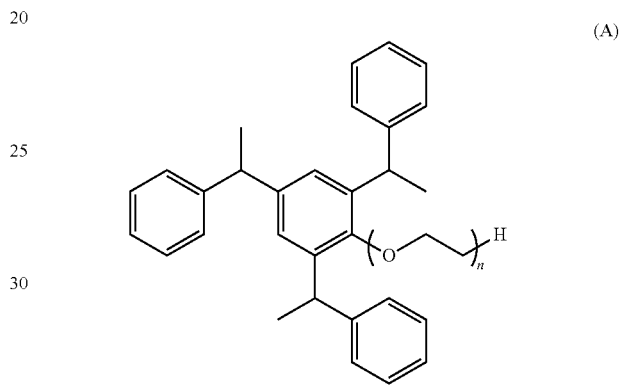

wherein n is 6-60.

2. The method of claim 1 wherein $R^1$ and $R^2$ are independently at each occurrence $C_1$-$C_6$ alkyl; and $R^3$ is independently at each occurrence H or $C_1$-$C_6$ alkyl.

3. The method of claim 1 wherein $R^1$ at each occurrence is $C_1$-$C_3$ alkyl.

4. The method of claim 1 wherein $R^2$ at each occurrence is $C_1$-$C_3$ alkyl.

5. The method of claim 1 wherein $R^3$ at each occurrence is H.

6. The method of claim 1 wherein the compound of formula I is: 2,2'-((2-hydroxytrimethylene)-diimino)bis(2-methyl-1-propanol), 2,2'-(2-hydroxypropane-1,3-diyl)bis(azanediyl) bis(2-methylpropane-1,3-diol), or 2,2'-(2-hydroxypropane-1,3-diyl)bis(azanediyl)dipropane-1,3-diol.

* * * * *